(12) United States Patent
Kimura et al.

(10) Patent No.: US 7,521,433 B2
(45) Date of Patent: Apr. 21, 2009

(54) GENE CARRIERS WITH THE USE OF POLYSACCHARIDE AND PROCESS FOR PRODUCING THE SAME

(75) Inventors: Taro Kimura, Dazaifu (JP); Masami Mizu, Sakai (JP); Kazuo Sakurai, Himeji (JP); Seiji Shinkai, Fukuoka (JP); Kazuya Koumoto, Kurume (JP)

(73) Assignees: Japan Science and Technology Agency, Tokyo (JP); Mitsui Sugar Co., Ltd., Saitama (JP); Fukuoka Prefectural Government, Fukuoka (JP)

( * ) Notice: Subject to any disclaimer, the term of this patent is extended or adjusted under 35 U.S.C. 154(b) by 321 days.

(21) Appl. No.: 10/471,366

(22) PCT Filed: Mar. 11, 2002

(86) PCT No.: PCT/JP02/02228

§ 371 (c)(1),
(2), (4) Date: Sep. 10, 2003

(87) PCT Pub. No.: WO02/072152

PCT Pub. Date: Sep. 19, 2002

(65) Prior Publication Data

US 2006/0084149 A1 Apr. 20, 2006

(30) Foreign Application Priority Data

Mar. 13, 2001 (JP) .............................. 2001-069655
Apr. 27, 2001 (JP) .............................. 2001-130705

(51) Int. Cl.
*A61K 31/716* (2006.01)
*C07H 15/04* (2006.01)

(52) U.S. Cl. ..................... 514/54; 536/123.12
(58) Field of Classification Search ................ 424/488, 424/646; 514/21, 31
See application file for complete search history.

(56) References Cited

U.S. PATENT DOCUMENTS 5,554,386 A * 9/1996 Groman et al. ............. 424/488

FOREIGN PATENT DOCUMENTS

WO    WO 01/07486    * 2/2001

OTHER PUBLICATIONS

Adachi, Y., Miura, N., et. al Enzyme immunoasay system for estimating the ultrastructure of (1,6)-branched (1,3)- β-glucans, Carbohydrate Polymers 39, 1999, 225-229.*
Mizu et. al., Chem. Commun., Feb. 2001, 429-430.*
Koumoto et al., "Chemical modification of schizophyllan by introduction of a cationic charge into the side chain which enhances the thermal stabiltiy of schizophyllan-poly(C) complexes" Chemical Communications (2001) pp. 1962-1963.*
Mizu et al., "Thermally induced conformational-transition of polydeoxyadenosine in the complex with schizophyllan and the baselength dependence of its stability" Chemical Communications (2001) pp. 429-430.*
George Y. Wu, Catherine H. Wu., *Receptor-Mediated in Vitro Gene Transformation by a Soluble DNA Carrier System*, The Journal of Biological Chemistry, vol. 262, No. 10, Issue of Apr. 5, pp. 4429-4432, 1987.
A.Steinbuchel, *Biopolymers*, vol. 5, Polysaccarides I, pp. 137-138, 2002.
A.Steinbuchel, *Biopolymers*, vol. 6, Polysaccarides II, pp. 64, 164-164, 2002.

* cited by examiner

*Primary Examiner*—Shaojia Anna Jiang
*Assistant Examiner*—Eric S Olson
(74) *Attorney, Agent, or Firm*—Fay Sharpe LLP

(57) ABSTRACT

Disclosed are gene carriers utilizing β-1,3-glucan and methods of preparing the same. The β-1,3-glucan has at least one 1,6-glucopyranoside branch and is chemically modified through periodate oxidation and reductive amination so as to impart nucleic acid-binding functional groups (for example, cationic functional groups) to at least some of the 1,6-glucopyranoside branches thereof. Triple helix β-1,3-glucan is dissolved in a polar organic solvent to form single-stranded β-1,3-glucan. By replacing, in the presence of a nucleic acid, the polar organic solvent for the solution containing the chemically modified single-stranded β-1,3-glucan by water, a complex (gene carrier) is formed in which the nucleic acid is bound to double-stranded β-1,3-glucan.

5 Claims, 7 Drawing Sheets

FIG. 1
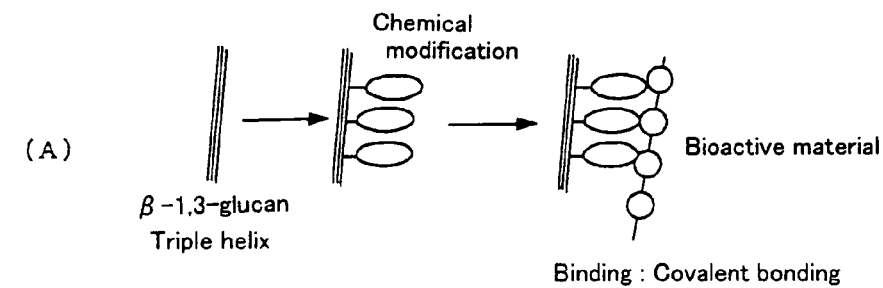
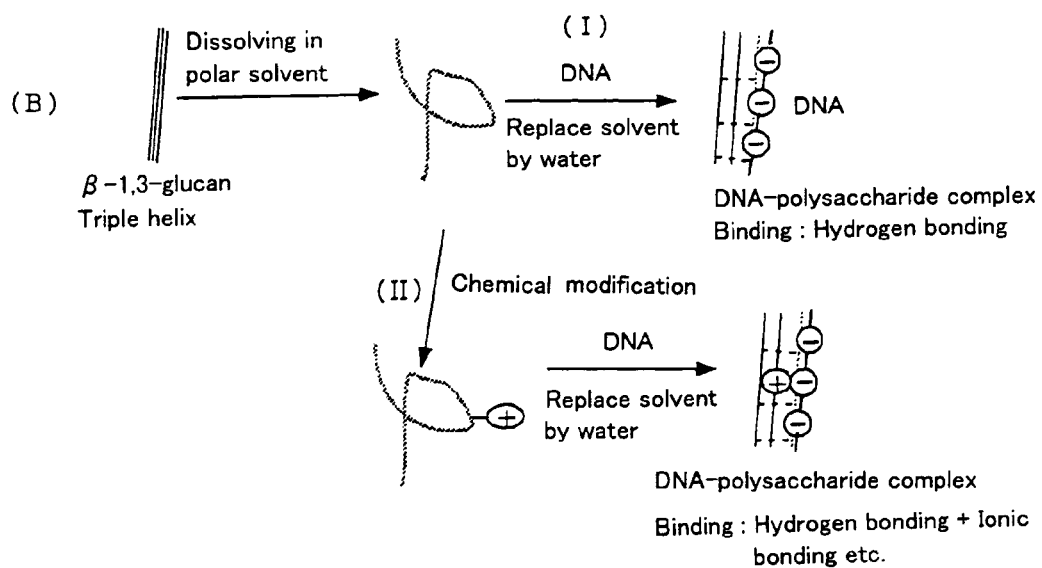
FIG. 2
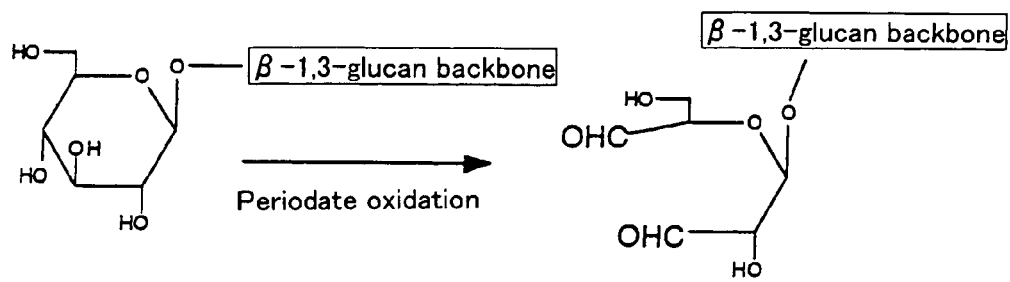

FIG. 6
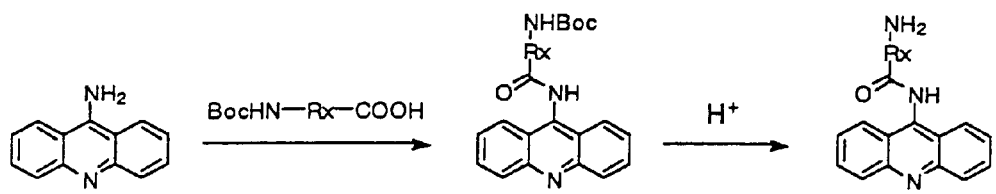
FIG. 7
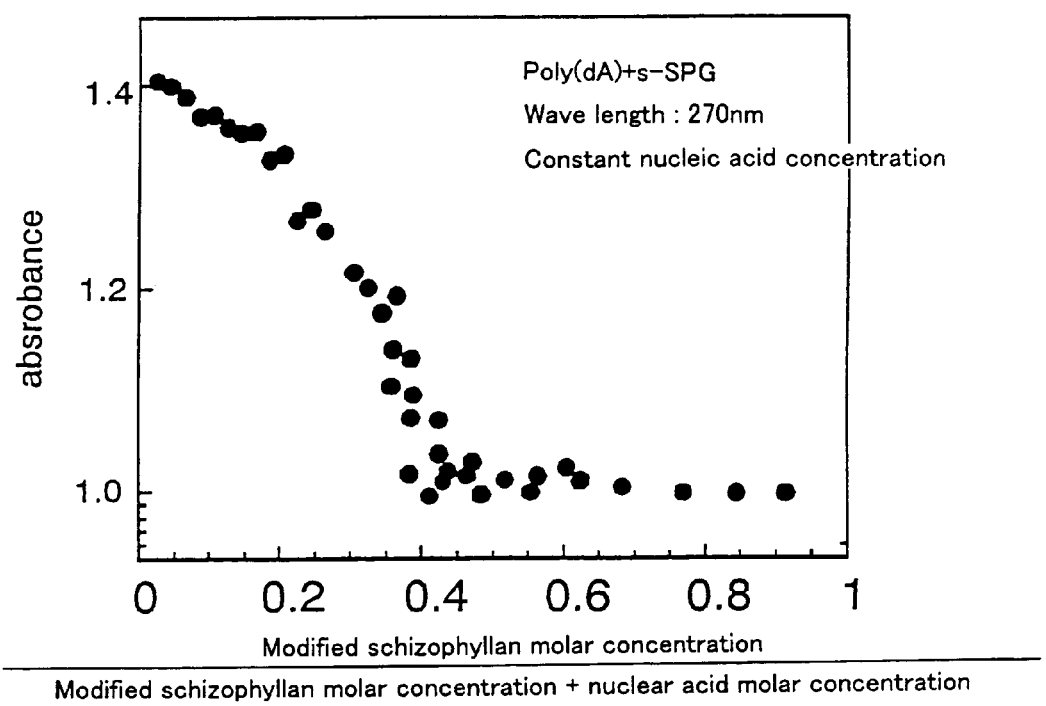
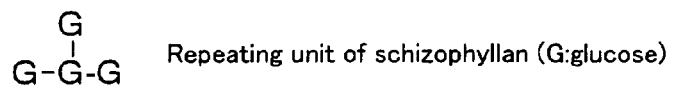

FIG. 8
- ● poly(C)
- ■ poly(C) + unmodified schizophyllan
- ▲ poly(C) + 2.5% amino group-modified schizophyllan
- ◆ poly(C) + 17% amino group-modified schizophyllan
- ★ poly(C) + 37% amino group-modified schizophyllan
- × poly(C) + polyethyleneimine

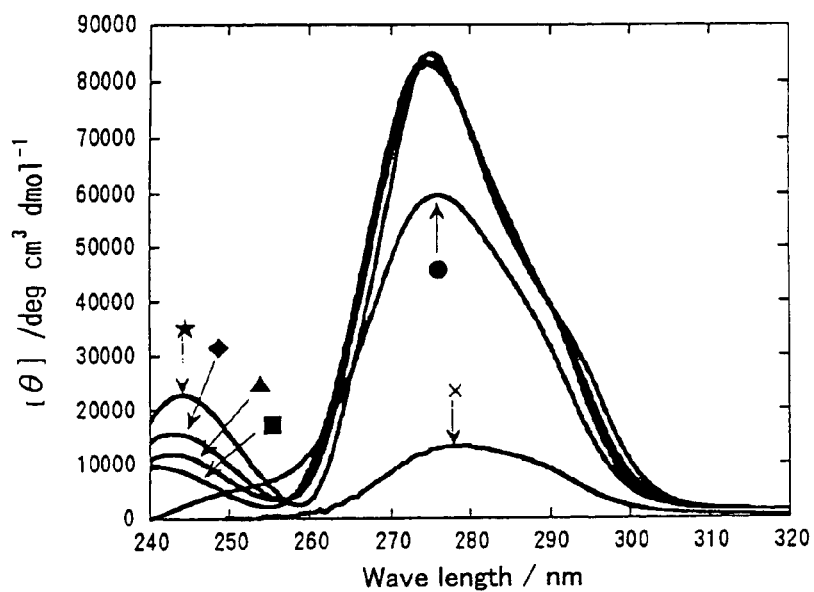

FIG. 9
- ● poly(C)
- ■ poly(C) + unmodified schizophyllan
- ▲ poly(C) + 2.5% amino group-modified schizophyllan
- ◆ poly(C) + 17% amino group-modified shizophyllan
- ★ poly(C) + 37% amino group-modified shizophyllan

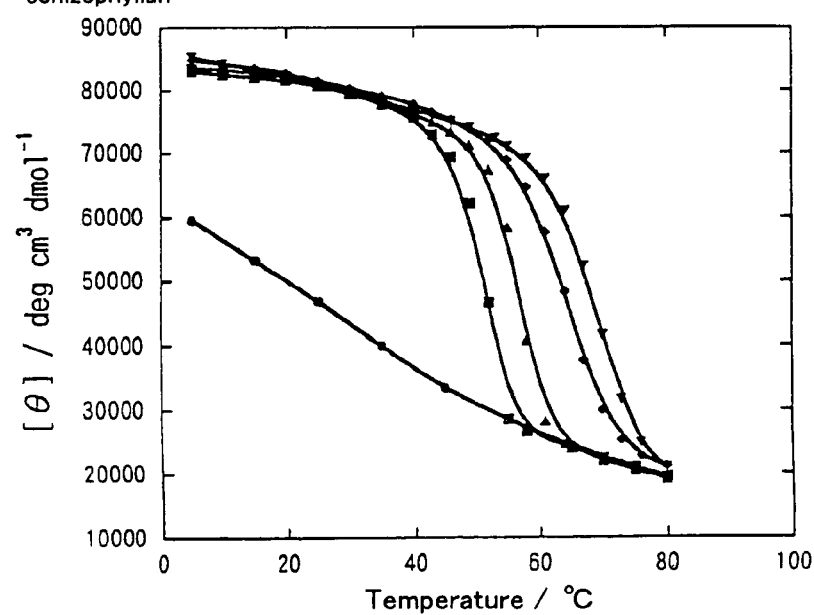

GENE CARRIERS WITH THE USE OF POLYSACCHARIDE AND PROCESS FOR PRODUCING THE SAME

This application is a national stage application of PCT/JP02/02228,filed Mar. 11, 2002, which claims priority to foreign applications JP2001-069655, filed Mar. 13, 2001, and JP2001-130705, filed Apr. 27, 2001.

TECHNICAL FIELD

The present invention relates to a gene carrier composed of a complex of a polysaccharide combined with a nucleic acid, and more particularly to a novel artificial material (compound) which is capable of interacting with a nucleic acid to form a complex with the nucleic acid for carrying the nucleic acid for use as an antisense agent and other applications.

BACKGROUND ART

The analysis of the human genome is expected to be completed in the early twenty-first century. For effective utilization of the outcome of the analysis, it is indispensable to develop a new technology for artificial manipulation of nucleic acids (carrying, sequence recognition, and control of transcription or translation of nucleic acids). The most important material for manipulating nucleic acids is considered to be a carrier capable of interacting with a nucleic acid such as DNA to support or carry the nucleic acid. However, in-vivo uses of conventional gene carriers composed of artificial materials have produced no significant results in human clinical studies. This can be attributed especially to (1) low gene-transferring efficiency, (2) difficulty in controlling the association and dissociation of genes (Cotton et al., Meth. Enzymol. 217: 618-644 (1993)); and (3) cytotoxity caused by cationic carrier materials (Choksakulnimitr et al., J. Control. Rel., 34: 233-241 (1995)).

Although viruses such as retroviruses (Miller, Nature 357: 455-460 (1992)) or adenoviruses (Mulligan, Science 260: 926-932 (1993)) have shown very promising in-vitro results as gene carriers, in-vivo use of these naturally occurring materials is restricted, especially because of inflammatory action, immunogenetic properties or the risk of integration into the genome or mutagenesis induction due to the viruses (Crystal, Science 270: 404-410 (1995)). Thus, as a substitute for such naturally-originating gene vectors, there has been proposed use of non-viral carriers composed of an artificial material which can be handled in an easier manner and can carry DNAs into the cells in a more efficient manner as compared with the viruses (Tomlinson and Rolland, J. Contr. Rel., 39: 357-372 (1996)).

At present, it is polyethyleneimine (PEI) that is the most extensively studied non-viral, artificial carrier material. It has been shown that PEI, a cationic polymer assuming a three dimensional branched structure, may result in transfection in a considerably highly efficient manner for various adhesive and floating cells, (Boussif et al., Gene Therapy 3: 1074-1080 (1996)). For example, 95% in-vitro transfection was accomplished in the 3T3 fibroblast cell line. In-vivo gene transfection into mouse brain using PEI as a carrier resulted in long-term expressions of the reporter gene and Bcl 2 gene in the neuron and the glial cell, the results being comparable to those obtained with the gene transfection using the adenovirus (Abdallah et al., Hum. Gene Ther. 7: 1947-1954 (1996)).

However, the safety of cationic polymers such as polyethylimine has not yet been established. While the introduction of amino groups is indispensable for imparting a cationic charge to such a polymer, an amino group has a risk of toxicity in the living body due to its high physiological activity. In fact, no cationic polymers studied so far have yet been put into practice, or yet been registered in the "Pharmaceutical Additives Handbook" (edited by the Pharmaceutical Additives Association of Japan and published by Yakujinipposha Publishing Co.).

β-1,3-glucan is a polysaccharide which has been clinically put to practical use as an intramuscular injection. It has been known since a long time ago that the polysaccharide takes, as it occurs naturally, a triple-stranded helix structure (cf., for example, Theresa M. McIntire, David A. Brant, J. Am. Chem. Soc., Vol. 120, 6909 (1998)). This polysaccharide has already been confirmed with respect to its in-vivo safety, based on the results of practical use for some 20 years as an intramuscular injection (Simizu et al., Biotherapy, Vol. 4, 1390 (1990); Hasegawa, Oncology and Chemotherapy, Vol. 8, 225 (1992)).

PCT/US95/14800 teaches that β-1,3-glucan is chemically modified so as to be capable of forming a conjugate with a bioactive material such as DNA, for use as a gene carrier. However, this prior art describes nothing but a preparation of a β-1,3-glucan/bioactive material conjugate wherein the β-1,3-glucan is utilized as it occurs naturally, i.e. in the form of a triple-stranded helix structure, to form the conjugate through covalent coupling.

Recently, the present inventors and others have found that β-1,3-glucan can form, as it is artificially treated, a new type of complex with a nucleic acid (PCT/JP00/07875; Sakurai and Shinkai, J. Am. Chem. Soc., 122, 4520 (2000); Kimura, Koumoto, Sakurai and Shinkai, Chem. Lett., 1242 (2000)). More specifically, it has been found that the triple-stranded helix form, which the polysaccharide takes as it naturally occurs, can be unbound into separate single strands by dissolving the triple helix (triple-stranded helix) polysaccharide in a polar solvent. Thus, as the solution is added with a single-stranded nucleic acid and the solvent is replaced by water (as a renaturation process), there is formed a triple-stranded helix complex composed of a single-stranded nucleic acid and a double-stranded polysaccharide. The binding between the polysaccharide and the nucleic acid in the complex is considered to be primarily through hydrogen bonding. (K. Sakurai, R. Iguchi, T. Kimura, K. Koumoto, M. Mizu, and S. Shinkai, Polym. Preprints, Jpn., 49, 4054 (2000)). The energy of this binding is relatively small, resulting in an easy dissociation of the complex. It is necessary to render this complex more strongly affinitive with nucleic acids in order to utilize the complex as a gene carrier.

It is an object of the present invention to provide a new type of gene carrier which is capable of interacting with and bonding to a nucleic acid such as DNA and RNA, without destroying the nucleic acid, to form a water-soluble complex so as to be applicable under biological conditions, and which is also capable of dissociating the nucleic acid from the complex and rebonding to such nucleic acid when necessary.

DISCLOSURE OF THE INVENTION

The present inventors discovered, through extensive studies for accomplishing the above-mentioned object and that led to the present invention, that introduction of nucleic acid-binding functional groups into β-1,3-glucan can make the polysaccharide highly interactive with a nucleic acid such as DNA and RNA so as to form a nucleic acid-polymer complex which is suitable for use in carrying genes, the separation of nucleic acids, or the controlling of the transcription or translation.

Thus, according to the present invention there is provided a method of preparing a gene carrier composed of a complex in which a single-stranded nucleic acid is bound to a double-stranded β-1,3-glucan wherein the β-1,3-glucan has at least one 1,6-glucopyranoside branch per repeating unit of polysaccharide, comprising the steps of (i) chemically modifying β-1,3-glucan so as to impart nucleic acid-binding functional groups to at least some of the 1,6-glucopyranoside branches thereof, (ii) dissolving triple helix β-1,3-glucan in a polar organic solvent to form single-stranded β-1,3-glucan, and (iii) replacing, in the presence of a nucleic acid, the polar organic solvent for the solution containing the single-stranded β-1,3-glucan by water so as to form the complex in which the single-stranded nucleic acid is bound to the double-stranded β-1,3-glucan.

According to the present invention there is also provided a gene carrier composed of a complex in which a single-stranded nucleic acid is bound to a double-stranded β-1,3-glucan wherein the β-1,3-glucan has at least one 1,6-glucopyranoside branch per repeating unit of polysaccharide, and wherein at least some of the 1,6-glucopyranoside branches are imparted with nucleic acid-binding functional groups. In a preferred embodiment of the present invention the nucleic acid-binding functional group is a cationic functional group, a steroid-based functional group, an amino acid-based functional group, or an intercalator-based functional group.

BRIEF DESCRIPTION OF THE DRAWINGS

FIG. 1 schematically shows a process of preparing the gene carrier of the present invention in comparison with that of the prior art.

FIG. 2 illustrates a reaction process by which the branch of β-1,3-glucan is subjected to a periodate oxidation in accordance with the present invention.

FIG. 6 illustrates a process of synthesizing an acridine derivative having a spacer for use as an intercalator-based functional group in the present invention.

FIG. 7 illustrates the results of a UV absorption experiment for stoichiometrically evaluating the complex of the present invention.

FIG. 8 shows a summary of CD spectra of the complexes of amino group (cationic functional group)-modified schizophyllan with poly(C) as well as those of unmodified schizophyllan or polyethyleneimine with poly(C) for comparison.

FIG. 9 illustrates temperature dependency of the CD spectra of the complexes of the amino group-modified schizophyllan and poly(C) as well as those of unmodified schizophyllan and poly(C) for comparison.

BEST MODE FOR CARRYING OUT THE INVENTION

Figure 3:
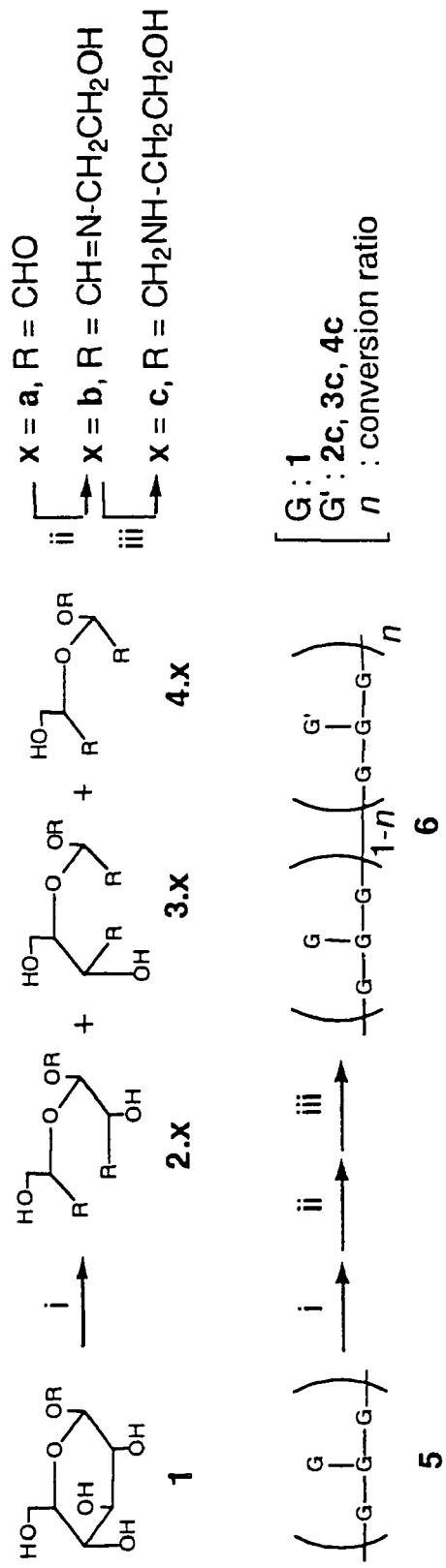
FIG. 3 illustrates a process by which the branch of β-1,3-glucan is imparted with cationic functional groups to yield the cationically modified polysaccharide in accordance with the present invention.

According to the present invention, β-1,3-glucan having a triple helix structure as it naturally occurs is artificially treated to provide a new type of gene carrier composed of a complex in which a target nucleic acid (DNA, RNA) is bound to double-stranded β-1,3-glucan.

FIG. 1 schematically shows the principle of the present invention in comparison with the prior art as described in PCT/US/9514800. FIG. 1(A) illustrates the gene carrier as described in PCT/US95/14800, in which triple helix β-1,3-glucan is chemically modified as it naturally occurs, and is bound with a target bioactive material such as an antisense DNA through hydrolysable covalent bonds. FIG. 1(B) relates to the idea conceived by the present inventors, in which triple helix β-1,3-glucan is dissolved in a polar organic solvent to form a single-stranded polysaccharide. (I) illustrates a complex disclosed in an earlier patent application by the present inventors (PCT/JP00/07875), in which the solvent for the solution containing the single-stranded β-1,3-glucan is directly replaced by water to form the nucleic acid-polysaccharide (double-stranded) complex. The binding energy for this complex is primarily due to hydrogen bonding and thus relatively small, which may lead to the problem of dissociation between the nucleic acid and the polysaccharide. This drawback is overcome by the process according to the present invention as illustrated in (II): A complex in which a target nucleic acid is bound to double-stranded β-1,3-glucan is formed by chemically modifying the branches (the side chains) of β-1,3-glucan to impart nucleic acid-binding functional groups thereto, subsequently dissolving the resultant β-1,3-glucan in a polar solvent, and finally replacing the solvent by water. The binding strength for this complex is due to the interactive actions (for example, ionic bonding) between the nucleic acid-binding functional group and the nucleic acid and therefore enhanced as compared with that of the complex shown in (I).

Thus, according to the present invention, β-1,3-glucan is once rendered into single-stranded form. The polysaccharide is then subjected to a renaturation process in water for forming double-stranded β-1,3-glucan during which process there emerge hydrogen-bonding sites within the polysaccharide. In the complex of the present invention, a nucleic acid is appropriately bound to the double-stranded β-1,3-glucan through the hydrogen-bonding sites and the nucleic acid-binding functional groups, and the nucleic acid may be released from the complex in a subsequent process (for example, the introduction of the complex into in-vivo or cultured tissue). By contrast, in the complex as described in PCT/US95/14800, a bioactive material such as nucleic acid is bond to triple helix β-1,3-glucan (in which there are no vacant hydrogen-bonding sites because the triple helix structure is constructed through the hydrogen-bonds) only through hydrolysable covalent bonds. The bioactive material can be released from the complex only under the conditions where hydrolysis occurs.

β-1,3-glucan is a generic term for polysaccharides in which glucose rings are linked by β-bonds through hydroxyl groups at the positions 1 and 3. The β-1,3-glucan to be used in the present invention is one which has at least one 1,6-glucopyranoside branch per repeating unit of polysaccharide. Examples of β-1,3-glucan having such structure for use in the present invention include, but are not limited to, schizophyllan, lentinan, pachyman, grifolan and sucleroglucan. β-1,3-glucan for use in the present invention may include a compound derived from chemical treatment of a natural β-1,3-glucan and having more than 10%, preferably more then 20% by weight, of the above-defined repeating units. Such β-1,3-glucan for use in the present invention is sometimes referred to herein to as "the polysaccharide of the present invention."

The "nucleic acid-binding functional group," as used herein, to be imparted to the 1,6-glucopyranoside branches of β-1,3-glucan for the present invention, refers to a functional group or atomic group which interacts with a nucleic acid so as to enhance binding (affinity) between the polysaccharide of the present invention and the nucleic acid. Suitable nucleic acid-binding functional groups for use in the present invention include cationic functional groups, steroid-based functional groups, amino acid-based functional groups and intecalator-based functional groups. Cationic functional groups imparted to the branches of the polysaccharide of the present invention can enhance the binding between the polysaccharide and the nucleic acid owing to electrostatic interaction with the negative charges on the nucleic acid such as DNA or RNA. Steroid-based functional groups or amino acid-based functional groups enhance the binding between the polysaccharide and nucleic acid, owing to hydrophobic interaction with the nucleic acid. Intercalator-based functional groups intercalate between the base-pairs of DNA or RNA and enhance the binding between the DNA or RNA and polysaccharide, owing to hydrogen bonding or hydrophobic interaction.

Cationic functional groups, particularly amino groups, may exhibit toxicity because of their physiological activity, depending upon the quantity of the functional groups. Amino groups are present innumerably in living organisms and an amino group is not itself toxic. The presence of an amino group in every repeating unit of polymer may often exhibit toxicity, as in polyethyleneimine which has been conventionally studied as an artificial carrier. The present invention features decreased introduction of nucleic acid-binding functional groups typified by cationic functional groups into the branches of β-1,3-glucan, so as to maintain the in-vivo safety of the polysaccharide to the utmost. Depending upon the types of nucleic acid-binding functional groups, the rate of introduction of nucleic acid-binding functional groups is determined based on three parameters: the toxicity, the releasability and the safety of the complex. The nucleic acid releasability and the complex stability depend upon the sequence and the number of bases of the target DNA In the present invention nucleic acid-binding functional groups are introduced generally at a rate of 50% or less, preferably 30% or less, more preferably 15% or less, and the most preferably 10% or less, based on the mole % of the repeating unit of the polysaccharide of the present invention.

It is generally known that the introduction of cationic functional groups into polyethyleneimine (PEI) at a rate of 10% or less will result in loss in the stability of PEI-nucleic acid complex. This is because the complex is formed only by electrostatic forces between the ion pairs. In the present invention the formation of the complex is essentially due to the hydrogen-bonding (plus the hydrophobic interaction) between the polysaccharide and the nucleic acid, while the binding between the nucleic acid-binding functional group and the nucleic acid serves as a trigger for the formation of the complex. This is evidenced from the fact that the CD spectrum of the complex of the polysaccharide of the present invention chemically modified with cationic functional groups and the nucleic acid is not different from that of the complex of the unmodified polysaccharide and the nucleic acid, as shown in Example 3 and Comparative Example 2. By contrast, in the case of polyethyleneimine, the complex therefrom exhibits a highly decreased CD spectrum in which there is observed no conformation resulting from the nucleic acid, as shown in Comparative Example 4. Thus, the gene carrier of the present invention, in which β-1,3-glucan is imparted with nucleic acid-binding functional groups on its branches, is essentially different from the conventional polycationic vector.

While the molecular weight of β-1,3-glucan for use in the present invention may vary depending upon the specific purpose of use, it is preferably 2000 or more in terms of weight-average molecular weight. A polysaccharide having a too-low molecular weight will not work as a polymer and make formation of the complex difficult.

A characteristic feature of the method for preparing the complex for use as a gene carrier according to the present invention is that it includes a step of forming a single-stranded polysaccharide, by dissolving triple helix β-1,3-glucan having the above-defined branches in a polar solvent. While any polar organic solvent may be used so long as it can unbind the triple helix, preferred examples include dimethyl sulfoxide, dimethyl formamide, tetrahydrofuran, propylene carbonate, methylene carbonate, and sulfolane, in which dimethyl sulfoxide and dimethyl formamide are more preferred. While the triple helix can be unbound simply by dissolving β-1,3-glucan for use in the present invention in such polar organic solvent, a heating procedure may be added if necessary. The unbinding of the triple helix may be carried out by dissolving it in an alkaline solution having a pH of 10 or higher, preferably 12 or higher, depending upon the specific purpose of use. Alternatively, a neutral aqueous solution containing β-1,3-glucan may be heated at a temperature of 100° C. or higher, preferably 120° C. or higher in an autoclave. The unbinding of the triple helix into the single strands can be ascertained by measuring the molecular weight using GPC (gel permeation chromatography), the light scattering method or the sedimentation equilibrium method in order to determine that the molecular weight has become one-third owing to unbinding.

A further characteristic feature of the method for preparing the complex for use as a gene carrier of the present invention is that it includes the step of chemically modifying the polysaccharide of the present invention, i.e. β-1,3-glucan having at least one 1,6-glucopyranoside branch per repeating unit of polysaccharide, so as to impart the above-defined nucleic acid-binding functional groups to at least some of said 1,6-glucopyranoside branches.

Any ordinary method known in the field of organic chemistry can be employed for chemically modifying the polysaccharide of the present invention so as to impart nucleic acid-binding functional groups thereto. For example, a general organic reaction may be applied, such as Williamson reaction or addition reaction to hydroxyl groups, addition reaction or condensation reaction to aldehydes or carboxylic acids produced by the oxidation of hydroxyl groups, or Williamson reaction following the activation (e.g. halogenation, tosylation or mesylation) of hydroxyl groups. Reductive amination onto the reducing terminal of the saccharide chain or aminolysis of lactone produced by the oxidation of the reducing terminal may also be applied.

Of these methods, the most preferred comprises periodate-oxidizing the 1,6-glucopyranoside branches of the polysaccharide of the present invention and then reductive-aminating the periodated 1,6-glucopyranoside branches to impart nucleic acid-binding functional groups. The periodate-oxidation and the reductive-amination may be conducted on the single-stranded 6-1,3-glucan formed by dissolving the natural polysaccharide in a polar organic solvent as explained earlier with reference to FIG. 1. Alternatively, the periodate-oxidation may be conducted on the triple helix β-1,3-glucan while the reductive-amination may be carried out on the single-stranded β-1,3-glucan. Still alternatively, both the periodate-oxidation and the reductive-amination may be conducted on the triple helix β-1,3-glucan.

Periodate oxidation, as used herein, is a reaction that converts a 1,2-diol quantitatively to the corresponding aldehyde, in which any alkali metal periodate can be used as the reagent, including sodium periodate, potassium periodate and rubidium periodate. Of such periodates, sodium periodate is most preferably used from the viewpoint of solubility and cost. Any polar solvent can be used for the reaction when the reaction is applied to the polysaccharide of the present invention, so long as it can dissolve the polysaccharide and does not adversely affect the reaction. In this respect, water is preferable.

When the periodate oxidation is conducted on single-stranded β-1,3-glucan formed by dissolving the starting polysaccharide in a polar organic solvent, it is convenient to use as a solvent for the periodate oxidation the same solvent as that used in the process for forming the single-stranded polysaccharide, dimethyl sulfoxide being particularly preferred. While the temperature for the periodate oxidation is not particularly limited unless the autodecomposition of the periodate should proceed, the reaction is generally carried out at a temperature in the range of 0 to 50° C.

Thus, as illustrated in FIG. 2, the bond between the 3- and 4-positions or between the 2- and 3-positions in the 1,6-glucopyranoside branch of β-1,3-glucan is cleaved to convert the hydroxyl group at these positions to aldehyde groups. As mentioned previously, a periodate oxidation features a selective reaction onto the C—C bond between diols at the 1- and 2-positions. Since β-1,3-glucan contains no 1,2-diols within its backbone, in the process of the reaction according to the present invention, there occurs no cleavage or modification on the backbone of the polysaccharide.

The β-1,3-glucan having the aldehyde groups within its branches as prepared above is then subjected to a reductive amination so as to impart nucleic acid-binding functional groups to the branches. The "reductive amination", as used herein, refers to a reaction in which a condensation reaction between an aldehyde and an amino group is followed by a reduction, as a measure for introducing a functional group through a covalent bond. While this reaction can be applied to any compound having a primary or secondary amine moiety or a hydrazine moiety, it is preferable to avoid a compound having a functional group, which may be affected by the reduction reaction, for example, vinylketone. A reducing agent for the reduction reaction can be selected from among sodium borohydride, lithium borohydride and sodium hydrocyanide. While any solvent can be used for the reaction when the reaction is applied to the polysaccharide of the present invention so long as it can dissolve the polysaccharide and does not adversely affect the reaction, the most preferred is water or dimethyl sulfoxide.

Thus, in the present invention, the 1,6-glucopyranoside branches, which have been imparted with nucleic acid-binding functional groups through the chemical modification comprising the periodate oxidation and the reductive amination, can be expressed by the following general formula (1). In formula (1), the two X's are generally identical nucleic acid-binding functional groups, but may be different nucleic acid-binding functional groups.

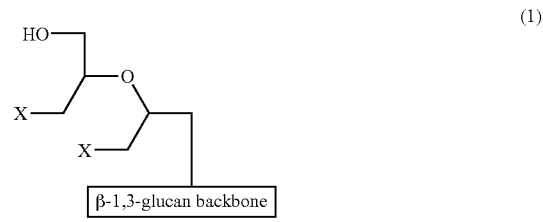

(1)

As will be understood from the foregoing, the nucleic-acid binding functional groups to be imparted to the 1,6-glucopyranoside branches of β-1,3-glucan by the reductive amination following the periodate oxidation according to the preferred embodiment of the present invention are those derived from a compound which contains a primary or secondary amine moiety or a hydrazine moiety to which the reductive amination can be applied.

Examples of the cationic functional groups suitable for use in the present invention include, but are not limited to, those derived from the following chain or cyclic compounds which contain at least one primary or secondary amino group. These compounds can be easily synthesized from commercially available compounds containing an amino group or groups.

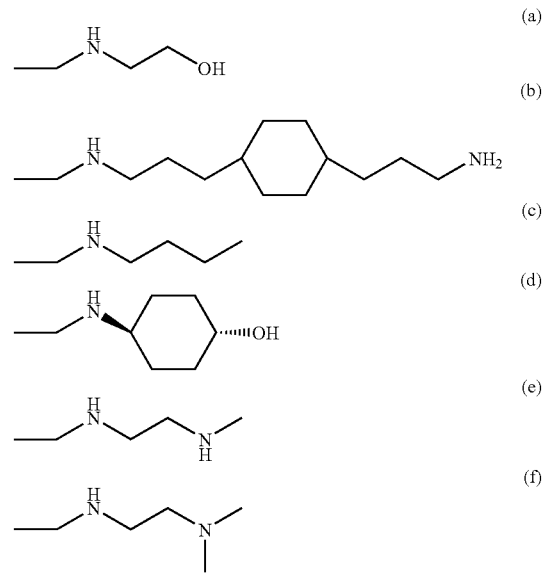

FIG. 3 illustrates an example of a process for preparing the chemically modified polysaccharide, by imparting to the branch the cationic functional groups as the nucleic acid-binding functional groups according to the present invention. In the figure, (i) denotes the step of the oxidation with a periodate, (ii) denotes the step of the formation of a Schiff base, and (iii) denotes the step of the reduction of the Schiff base with sodium borohydride. In the case of β-1,3-glucan having branches containing an unreacted hydroxyl group at the 3-position, there are obtained products as expressed by 2.X, 3.X, and 4.X. The reactions occur at the branch or side chain as shown by 5 and 6 in the figure.

The steroid-based functional groups to be imparted to the branches of the polysaccharide of the present invention by the reductive amination following the periodate oxidation are preferably those derived from the compounds expressed by the following formula (2):

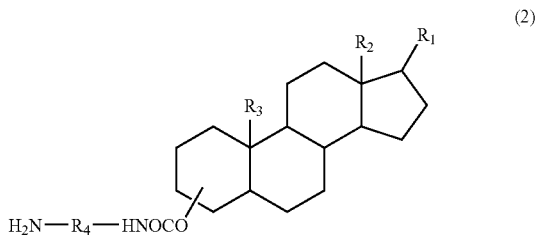

In the formula, $R_1$, $R_2$ and $R_3$ independently express hydrogen atom or a substituent containing carbon, oxygen, nitrogen and/or hydrogen atom(s). $R_4$ denotes a spacer moiety which is hydrogen atom or is derived from a chain or cyclic compound containing carbon, oxygen, nitrogen and/or hydrogen atom(s). The atomic group containing $R_4$ may be bound to any position of the steroid ring. A compound falling outside the above-mentioned general formula (1) may also be used, provided that it contains a steroid ring, as exemplified by a corticosterone or cortisol derivative.

Figure 4:
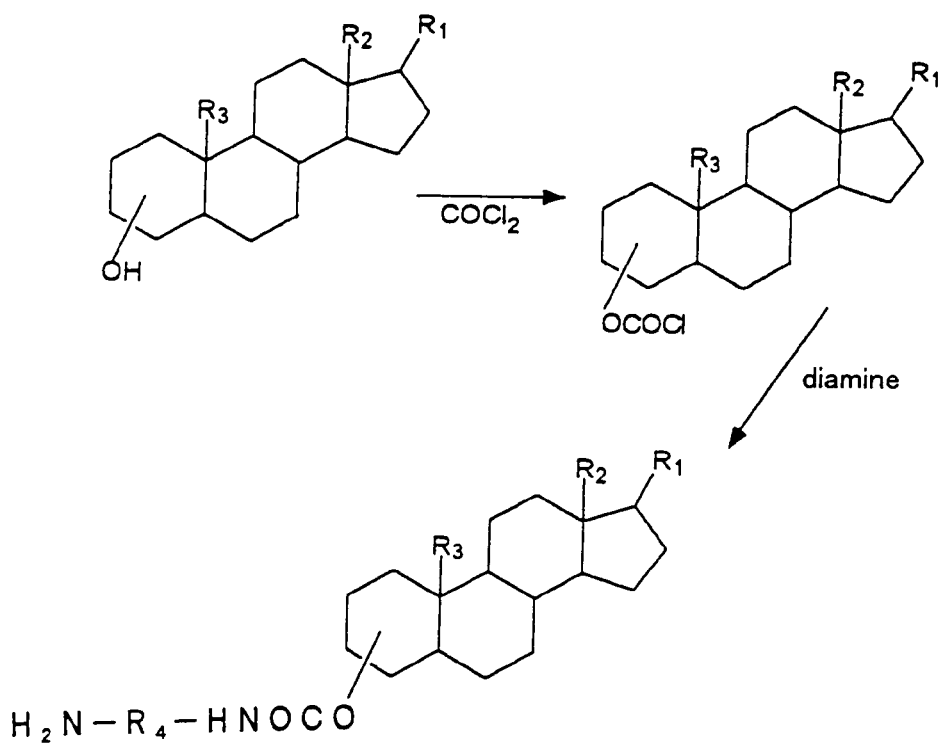
FIG. 4 illustrates a process of synthesizing a compound providing a steroid-based functional group for use in the present invention.

Such compounds may be prepared in accordance with a reaction scheme as shown in FIG. 4 in which the hydroxyl group bound to the steroid ring is caused to react with a diamine. The compound is then subjected to the reductive amination as mentioned earlier to impart the steroid-based functional groups to the branches of the β-1,3-glucan.

The amino acid-based functional groups to be imparted to the branches of the β-1,3-glucan by the periodate oxidation and the reductive amination according to the preferred embodiment of the present invention are those derived from an amino acid as expressed by the following general formula (3) or from a peptide composed of a plurality of such amino acids:

In the formula, $R_5$ denotes the side chain of amino acid, including $CH_3$ (in the case of alanine), $CH_2Ph$ (in the case of phenylalanine, wherin Ph denotes a phenyl group), $(CH_3)_2CH$ (in the case of valine), $(CH_3)_2CHCH_2$ (in the case of leucine), $CH_2OH$ (in the case of serine), $CH_3(OH)CH$ (in the case of threonine), $CH_2$—SH (in the case of cysteine) and so on.

Figure 5:
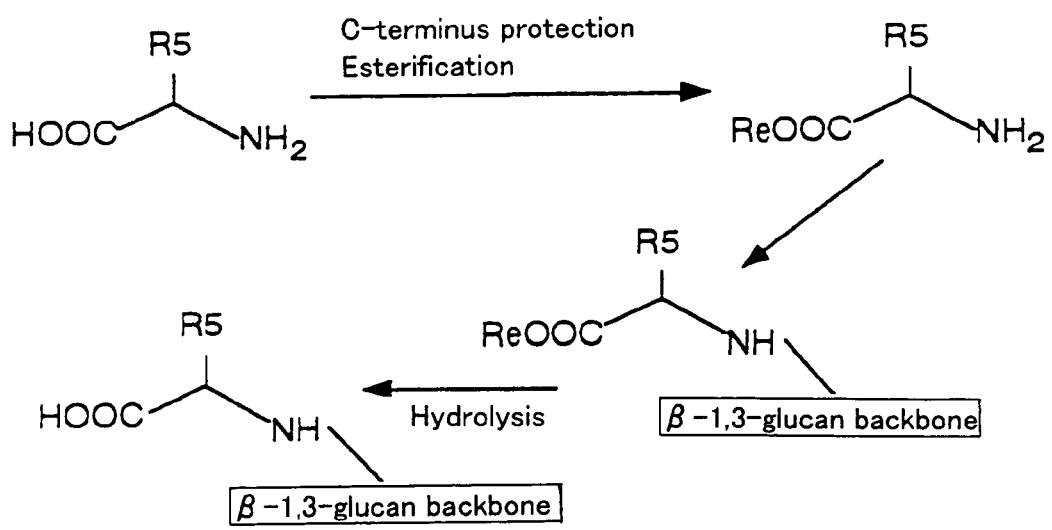
FIG. 5 illustrates a process by which an amino acid-based functional group is imparted to the branch of β-1,3-glucan.

The amino acid-based functional groups derived from an amino acid as expressed by the formula (3) are introduced into the branches of β-1,3-glucan in accordance with a reaction scheme as shown in FIG. 5, in which the amino group of the amino acid is utilized for the introduction following the esterification of the amino acid. Without the esterification of the amino acid, the reductive amination would not be possible because an amino acid usually behaves as an amphoteric ion. In the case of lysine, arginine, aspartic acid or glutamic acid, it is also necessary to protect the side chain of the amino acid. The protection of amino acid side chain may be carried out in any manner known in the field of amino acid chemistry, for example, with reference to "Experimental Chemistry Series" (Maruzen Co.) or "Biochemical Experiments Series" (Tokyo-Kagaku-Dojin Co.).

The type of amino acid bound to the polysaccharide may vary depending upon the purpose of use. For example, for the purpose of enhancing the affinity with a nucleic acid due to the formation of an ion-pair, it is preferred to use a basic amino acid. For enhancing the transfection efficiency, it is preferred to use a hydrophobic amino acid such as arginine. While FIG. 5 illustrates the case where the N-terminus is bound directly to the branch (the side chain) of β-1,3-glucan, as a matter of convenience, there may be used an appropriate spacer moiety therebetween if necessary. The amino acid-based functional groups for use in the present invention may be derived from a peptide composed of a plurality of amino acids. Any peptide capable of interacting specifically with a nucleic acid may be used, including fibronectin, proteins selected from among the integrin family, integrin-binding peptides (cystein-tyrosine-glycine-glycine-arginine-glycine-aspartic acid-threonine-proline), DNA-interacting—peptide-complexed nucleic acid (PNA) and so on. They can be introduced into the branches of the polysaccharide in a similar manner as in the case of amino acid mentioned above.

The intercalator-based nucleic acid-binding functional groups to be imparted to the branches of the polysaccharide of the present invention by the reductive amination following the periodate oxidation in accordance with the preferred embodiment of the present invention are those from intercalating compounds containing an amino group or a carboxyl group. Preferred examples of such compounds include those containing an acridine, proflavin or ethidium moiety as expressed by the following formulae (4), (5), and (6), respectively.

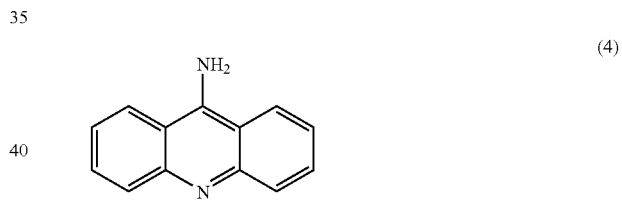

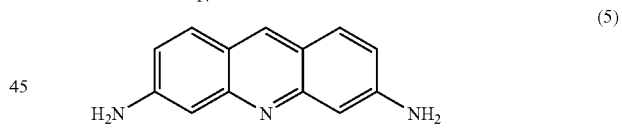

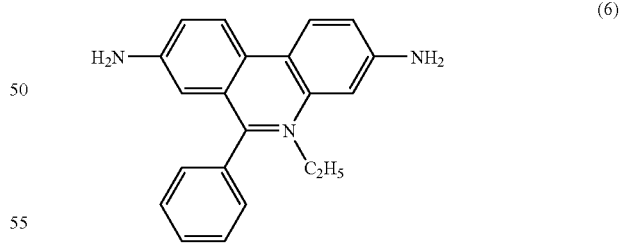

While it is possible to bind these compounds having an amino group, such as expressed by the formulae above, to the branches (the side chains) of the polysaccharide of the present invention by the reductive amination following the periodate oxidation, it is preferred for the compounds to have a spacer moiety so that they will be arranged at an appropriate distance from a nucleic acid such as DNA in interacting with it. A convenient method is to introduce an aminoalkane carboxylate through an amide bond with an appropriate condensation agent (for example, dicyclohexyl carbodiimide, cf. Experimental Chemistry Series, Maruzen Co.) FIG. 6 illustrates a process for the introduction of such a spacer moiety, acridine, as an example. The resultant is bound to the branches of β-1,3-glucan of the present invention by the reductive amination explained previously. When an intercalating compound containing a carboxyl group is used, a diamine having an appropriate spacer moiety is introduced with a condensation agent, in a manner similar to the aforesaid. The resultant is then bound to the branches of the polysaccharide of the present invention by the reductive amination.

The third characteristic feature of the method for preparing the gene carrier of the present invention is that it includes the step of replacing, in the presence of a nucleic acid, the polar organic solvent for the solution containing the single-stranded β-1,3-glucan, following the chemical modification, by water so as to form the complex in which the nucleic acid is bound to the double-stranded β-1,3-glucan. More specifically, in the process where the β-1,3-glucan taking the single-stranded form in the polar organic solvent will revert in water to the triple-stranded form (renaturation process), the presence of a nucleic acid results in the formation of a new complex composed of single-stranded nucleic acid plus double-stranded polysaccharide. While such regeneration process can be carried out by replacing the solvent with water generally through dialysis or ultrafiltration, simple dilution of the polar organic solvent with water will also work. It is further to be noted, as can be seen from the foregoing, that the replacement process of the polar organic solvent by water may be applied to any of single-stranded β-1,3-glucan obtained by the chemical modification comprising the periodate oxidation of the triple helix β-1,3-glucan, followed by the dissolution in the polar solvent and then the reductive amination; single-stranded β-1,3-glucan obtained by the chemical modification comprising dissolving the triple helix β-1,3-glucan in the polar organic solvent to prepare the single-stranded form, followed by the periodate oxidation and the reductive amination; and single-stranded β-1,3-glucan obtained by the chemical modification comprising the periodate oxidation and the reductive amination of the triple helix β-1,3-glucan, followed by the dissolution in the polar organic solvent.

The polysaccharide of the present invention thus prepared with the branches having been imparted with nucleic acid-binding functional groups is capable of interacting with a nucleic acid such as DNA or RNA and forming a complex with the nucleic acid. The formation of the complex can be confirmed by studying the conformational change, for example, by measuring the CD (circular dichroism) spectra.

The complex of the present invention composed of the double-stranded β-1,3-glucan and the nucleic acid bound to the branches of the polysaccharide through the nucleic acid-binding functional groups is usually water-soluble, and may undergo a dissociation and a rebinding due to temperature change and/or pH change. The binding capability thereof varies depending upon the chemical structure of the DNA or RNA (A, T, G, C, U). The complex has resistance to nuclease, so that no decomposition of the nucleic acids (genes) occurs. Thus, the complex of the present invention can be used as a gene carrier to manipulate various types of genes. A target gene (DNA or RNA), for example, an antisense nucleic acid, can be carried by the gene carrier of the present invention, in the form of the complex in which the nucleic acid is bound to the β-1,3-glucan, and introduced into in-vivo or cultured tissues. The present invention is therefore expected to contribute to the development of medicines and reagents for diagnostic and therapeutic purposes. The complex of the present invention may also be utilized as a nucleic acid-protecting agent since it has resistance to nuclease.

Various types of nucleic acids can be used in the preparation of the complex according to the present invention. For example, any antisense nucleic acid as described in "Idenshi-chiryo (gene therapy) R&D Handbook, N.T.S." is usable. Besides deoxyribonucleic acid, there may be used such nucleic acid as phosphorothioate nucleic acid, phosphoroamidate nucleic acid, peptide nucleic acid, purine ribose, and methoxy-ethoxy DNA. If necessary, the present invention can be applied to double-stranded DNA, in which the DNA is believed to bind partly to the polysaccharide of the present invention through the single-stranded region as in the bulge or bulge loop, although the detailed mechanism has not yet been elucidated.

EXAMPLES

The invention will be more fully described with reference to the following examples and comparative examples, which are only for exemplifying purposes and not for restricting the invention.

Example 1 shows a case where schizophyllan, a typical polysaccharide of the present invention, having a molecular weight of 150000, is imparted with cationic functional groups as the nucleic acid-binding functional groups. Example 2 set out a characterization (the molecular weight and the rate of introduction of the functional groups) of the cationic polysaccharide thus obtained. Example 3 and Comparative Examples 1 & 2 relate to measurements of CD spectra of complexes of the cationic polysaccharide with poly(C), a single-stranded RNA, demonstrating that the chemical modification according to the present invention resulted in no change in CD spectrum. Example 4 describes melting behaviors of the complexes, demonstrating the increased stability of the cationically modified polysaccharide based complex. Example 5 describes formation of complexes of the cationically modified polysaccharide, as compared with unmodified polysaccharide, with homogeneous nucleic acid other than poly(C), and an antisense DNA, a heterogeneous nucleic acid. Example 6 sets forth an experimental example to demonstrate that the gene carrier of the present invention, composed of the modified polysaccharide (schizophyllan) serves to carry an antisense DNA, thereby regulating the expression of a protein. Example 7 describes change in the regulation of the protein expression by the gene carrier for the antisense DNA as set forth in Example 6, with the elapse of time. Example 8 shows an example of an experiment for studying the resistance of the polysaccharide to a nuclease. Example 9 describes an experiment by which it is demonstrated that the carrier composed of the modified polysaccharide (schizophyllan) of the present invention serves to regulate the expression of a protein and is resistant to a nuclease. Example 10 is to show that the modified schizophyllan of the present invention is capable of forming a complex with a nucleic acid and the complex may undergo a dissociation in the presence of a complementary strand.

Example 11 describes synthesis of a polysaccharide of the present invention, which is imparted with steroid-based functional groups as the nucleic acid-binding functional groups. Example 12 describes synthesis of another polysaccharide of the present invention, which is introduced with peptides as the nucleic acid-binding functional groups. Example 13 sets forth synthesis of a further polysaccharide of the present invention, which is imparted with intercalator-based functional groups as the nucleic acid-binding functional groups. Example 14 is to demonstrate that the polysaccharide of the present invention as prepared in Example 11 is capable of forming complexes with a nucleic acid. Example 15 demonstrates that the polysaccharide of the present invention as prepared in Example 12 is capable of forming a complex with a nucleic acid and the complex can be introduced into hepatic cells. Example 16 is to demonstrate that the polysaccharide of the present invention as prepared in Example 1 is capable of forming a complex with a nucleic acid and the complex can be introduced into cancer cells.

Example 1

Synthesis of Cationic Polysaccharide (Amino Group-Modified Schizophyllan), by Chemical Modification with Cationic Functional Groups A polysaccharide of the present invention was synthesized in accordance with the reaction scheme as shown FIG. 3. It is possible to regulate the rate of introduction of amino group by regulating the equivalent number of sodium periodate for the periodate oxidation. The same method of synthesis is applicable regardless of the rate of introduction. The present example relates to the synthesis of cationic functional group-modified schizophyllan in which the schizophyllan is introduced with amino groups at a rate of introduction of approximately 2.5%, 17% or 37%. The amino group introduced was derived from 2-aminoethanol. It is possible to regulate the rate of introduction of the amino group by regulating the equivalent number of the sodium periodate with respect to the branching glucose moiety. The experimental results are shown in Example 2.

Triple helix schizophyllan was prepared in accordance with the conventional method as described in "A. C. S. 38(1), 253 (1997); Carbohydrate Research, 89, 121-135 (1981)): *Schizophyllum commune.* Fries (ATCC 44200) available from American Type Culture Collection was subjected to a stationary culture in a minimal medium for seven days. After removal of the cellular materials and insoluble residues, the supernatant was subjected to a supersonic treatment to yield schizophyllan of a triple helix structure having a molecular weight of 450000.

100 mg of the thus obtained schizophyllan was dissolved in 100 ml water. To the resultant solution was added slowly an aqueous solution of sodium periodate (in an equivalent of 4%, 40%, or 500% (an excess amount) based on the branching glucose of the schizophyllan) and stirring was performed for two days at 4° C. The reaction solution was subjected to dialysis through a membrane with an exclusion limit of 12000, followed by lyophilization. The white solid product was dissolved in 20 ml dimethyl sulfoxide, a polar organic solvent. To the resultant solution was added 2 ml 2-aminoethanol (an excess amount: more than 10000 equivalents) and then stirring was performed for two days at room temperature. Then, there was added 100 mg sodium borohydride, followed by stirring for one day at room temperature. After the excess sodium borohydride was deactivated with acetic acid, reprecipitation with methanol was conducted to yield the modified polysaccharide (schizophyllan) to which the cationic functional groups were imparted.

Example 2

Characterization of the Cationic Polysaccharide

Characterization of the polysaccharide imparted with the cationic functional groups as prepared in Example 1 was performed by measuring the molecular weight and the rate of introduction of the amino group. The molecular weight was examined through gel permeation chromatography (GPC) and also by measuring the viscosity. The molecular weight of the polysaccharide was found to be 150000, i.e., one third of that of the starting triple helix schizophyllan. The rate of introduction of the amino group was determined on microanalysis of nitrogen by elemental analysis (lower detection limit: 0.05%). The microanalysis of nitrogen was performed three times for each sample, with the upper and lower values being shown in the following table.

TABLE 1

| Periodate Equivalent | Nitrogen Content | Amino Group Introduction Rate |
|---|---|---|
| 4% | 0.09-0.12% | 2.1-2.8% |
| 40% | 0.69-0.75% | 16.3-17.8% |
| 500% | 1.15-1.54% | 35.2-37.4% |

Example 3

Interaction of Amino Acid-Modified Schizophyllan with Poly(C)

The thus-prepared schizophyllans modified with 2.5%, 17% and 37% of amino group (as the cationic functional group) were each dissolved in dimethyl sulfoxide, a polar organic solvent, to give a final concentration of 0.5 g/dL. To each resultant solution 100 μl, there were added pure water 900 μl, 10 mM Tris buffer 100 μL, and 0.1 g/L poly(C) (Pharmacia) solution 100 μl. The resultant mixtures were all clear, homogeneous solutions.

Comparative Example 1

Interaction of Unmodified (Natural) Schizophyllan with Poly(C)

A mixture was prepared in the same manner as in Example 3 using unmodified schizophyllan. The resultant mixture was a clear, homogeneous solution.

Comparative Example 2

Interaction of Polyethyleneimine with Poly(C)

A mixture was prepared in the same manner as in Example 3 using polyethyleneimine in place of schizophyllan. The resultant solution was turbid. The solutions as prepared in Example 3 and Comparative Examples 1 & 2 were each matured in a refrigerator overnight, and then subjected to CD spectrum measurement on a circular dichroism apparatus (Jasco) to confirm the formation of a complex.

FIG. 8 shows the CD spectrum data (at 5° C.) for Example 3 and Comparative Examples 1 & 2 in comparison with a system in which no polymeric material was present (i.e. only with poly(C)). The CD spectrum data were expressed in terms of molecular ellipticity (cf. Biochemical Experiments Series Vol. 2, Nucleic Acid Chemistry II, Edited by Biochemical Society of Japan, Tokyokagaku-Dojin Co.)

It was observed that a new band appeared at 245 nm and the CD spectrum intensity at 275 nm increased 1.5 times when the unmodified (natural) schizophyllan formed a complex with poly(C). With the 2.5%, 17% and 37% amino group-modified schizophyllans, there was observed a spectrum quite similar to that of the unmodified schizophyllan-poly(C) complex although the intensity at 245 nm slightly increased.

These spectral observations were highly reproducible suggesting that the spectral change is not due to unspecific adsorption based on cationic, electrostatic interactions and that the 2.5%, 17% and 37% amino group-modified schizophyllans forms a complex with poly(C) in a similar manner to the unmodified (natural) schizophyllan. With polyethyleneimine, there was observed a decrease in the CD spectrum intensity.

The stoichiometric analysis of the complex was made through UV absorption measurement: The 17% amino group-modified schizophyllan was dissolved in dimethyl sulfoxide to give a final concentration of 0.5 g/dL. The solution of the single-stranded polysaccharide thus obtained was added to 0.1 g/dL poly(dA) solution in 100 μL pure water to prepare solutions with varying molar ratios of the nucleic acid to the schizophyllan. Then 10 mM Tris buffer (pH 8.0) was added to make the nucleic acid concentration in the solution constant. The DMSO in the system was replaced by water through ultrafiltration. The disappearance of the DMSO was confirmed by UV absorption measurement at 230 nm. It was ascertained, through a preliminary experiment to measure changes in the weights of the solute and the solvent, that there occurred no change in the nucleic acid concentration during the process.

The samples were measured for the ultraviolet absorption spectra. The formation of the complex was examined through the hypochromic effect in the UV absorption (decrease in the absorbance due to the formation of the complex). The results are shown in FIG. 7, and demonstrate that there was formed a complex composed of 2 moles of the 6-1,3-glucan and 3 moles of the nucleic acid in terms of the number of moles of the repeating units (cf. the lower part of FIG. 7), i.e., that the complex was composed of the double-stranded polysaccharide plus the single-stranded nucleic acid.

Example 4

Melting Behaviors of Unmodified Schizophyllan and Amino Group-Modified Schizophyllan The solutions prepared in Example 3 and Comparative Example 1 were measured for the temperature dependence of the CD spectrum. FIG. 9 illustrates the data for the CD spectra at 275 nm in terms of molecular ellipticity plotted against the temperature. ● denotes data for the poly(C) alone, ■ for the poly(C) plus the unmodified schizophyllan, ▲ for the poly(C) plus the 2.5% amino group-modified schizophyllan, ♦ the poly(C) plus the 17% amino group-modified schizophyllan, and ▼ for the poly(C) plus the 37% amino group-modified schizophyllan, respectively.

As can be seen from FIG. 9, the complexes of the amino group-modified schizophyllans with the poly(C) show melting behaviors similar to the complex of unmodified (natural) schizophyllan with the poly(C). It was also demonstrated that the modified schizophyllan-based complexes were more stable in terms of the melting temperature (Tm) than the unmodified schizophyllan-based complex: by 7° C. for the 2.5% amino group-modified schizophyllan, 14° C. for the 17% amino group-modified schizophyllan, and as great as 20° C. for the 37% amino group-modified schizophyllan.

Example 5

Interaction of Amino Group-Modified Schizophyllan with Various Nucleic Acids

Study was made on the interaction of the 2.5% amino group-modified schizophyllan as prepared in Example 1 with various types of nucleic acids. The 2.5% amino group-modified schizophyllan was dissolved in dimethyl sulfoxide to give a final concentration of 0.5 g/dL. To 100 μl of the solution thus prepared, there were added 900 μl pure water, 100 μl of 10 mM Tris buffer (pH 8.0), and 100 μl of 0.1 g/dL nucleic acid solution. The resultant solutions were all clear and homogeneous.

The homogeneous nucleic acids used were poly(A) (Pharmacia), poly(U) (Yamasa), poly(G) (Sigma), poly(dA) (Pharmacia), poly(dT) (Pharamacia), poly(dC) (Pharmacia), and poly(dG) (Synthesized solid product). An antisense DNA was also used that was composed a sequence of CTTTAAGAAG-GAGATATACAT (SEQ ID NO:1), with the 3' end thereof being linked to forty dA's. The antisense DNA contained a sequence complementary to the sequence of GAAATTCT-TCCTCTATATGTA (sequence for the lysome binding site of T7 promoter carried by T7 phage).

These nucleic acids were measured for the melting curve in the same manner as in Example 4. With all the nucleic acids, the spectral curve for the 2.5% amino group-modified schizophyllan is quite similar to that for the unmodified schizophyllan except for an observed increase in the melting temperature in the former. The values for melting temperature obtained from the melting curves are shown in Table 2.

TABLE 2

| Nucleic acid | Melting temperature (Tm) | | |
|---|---|---|---|
| | Unmodified schizophyllan | 2.5% amino group-modified schizophyllan | Δ Tm |
| poly(A) | 30° C. | 33° C. | 3° C. |
| poly(U) | * | 17° C. | |
| poly(G) | * | * | |
| poly(dA) | 70° C. | 80° C. | 10° C. |
| poly(dC) | * | 17° C. | |
| poly(dT) | 16° C. | 18° C. | 2° C. |
| poly(dG) | * | * | |
| Antisense | 33° C. | 38° C. | 5° C. |

* No complex formation

Example 6 and Comparative Examples 3 & 4

Antisense Effect Test

With the 2.5% amino group-modified schizophyllan as prepared in Example 1 (this modified schizophyllan of the present invention is sometimes referred to as SPG in this Example and Examples 7 through 10), a test for antisense effect was conducted using a well-known cell-free system in which transcription and translation reactions proceed in a cellular extract from *E. Coli* T7 S30. As an indication of antisense effect, a template was employed composed of a plasmid pQBI63 (Takara Shuzo) encoding GFP (Green Fluorescence Protein) which is a fluorescent protein and widely used as a reporter gene. For the transcription and translation reactions, there was used *E. coli* T7 S30 in-vitro transcription/translation kit (Promega). The antisense chain contained a sequence CTTTAAGAAGGAGATATACAT (SEQ ID NO:1), as describe in Example 5, with the 3' end thereof being linked to forty dAs. To the antisense DNA was added the modified schizophyllan of the present invention (SPG) in an amount of 0.1, 0.25, 0.5, 0.75, 1.0, 2.0, 3.0, or 5.0-fold on a molar basis, in the manner described in Example 5. The resultant solutions were matured in a refrigerator for five days, and then subjected to ultrafiltration with a membrane having an exclusion limit of 3000 to remove the dimethyl sulfoxide (Example 6).

To the antisense DNA was added polyethyleneimine (PEI) in an amount of 0.1, 0.5, 1.0, 5, 10, or 50-fold on a molar basis, for the purpose of comparison (Comparative Example 3). For the purpose of further comparison, the influence of the modified schizophyllan alone was also studied with schizophyllan samples prepared by dialyzing (in distilled water) the schizophyllan as used in Example 5 with a membrane having an exclusion limit of 12000 (Comparative Example 4).

The reaction solutions were prepared by adding the antisense DNA, the SPG complexes, the PEI complexes, or the schizophyllan samples to the mixture containing the template DNA and the transcription/translation solution. Each of the reaction solutions was allowed to undergo the transcription and translation reactions by being kept at 37° C., followed by the measurement of fluorescence emitted by GFP in the reaction solution (with a device from Hitachi). The data were normalized in such way that the fluorescence intensity at 507 nm with the solution not containing the antisense DNA was 100.

Figure 10:
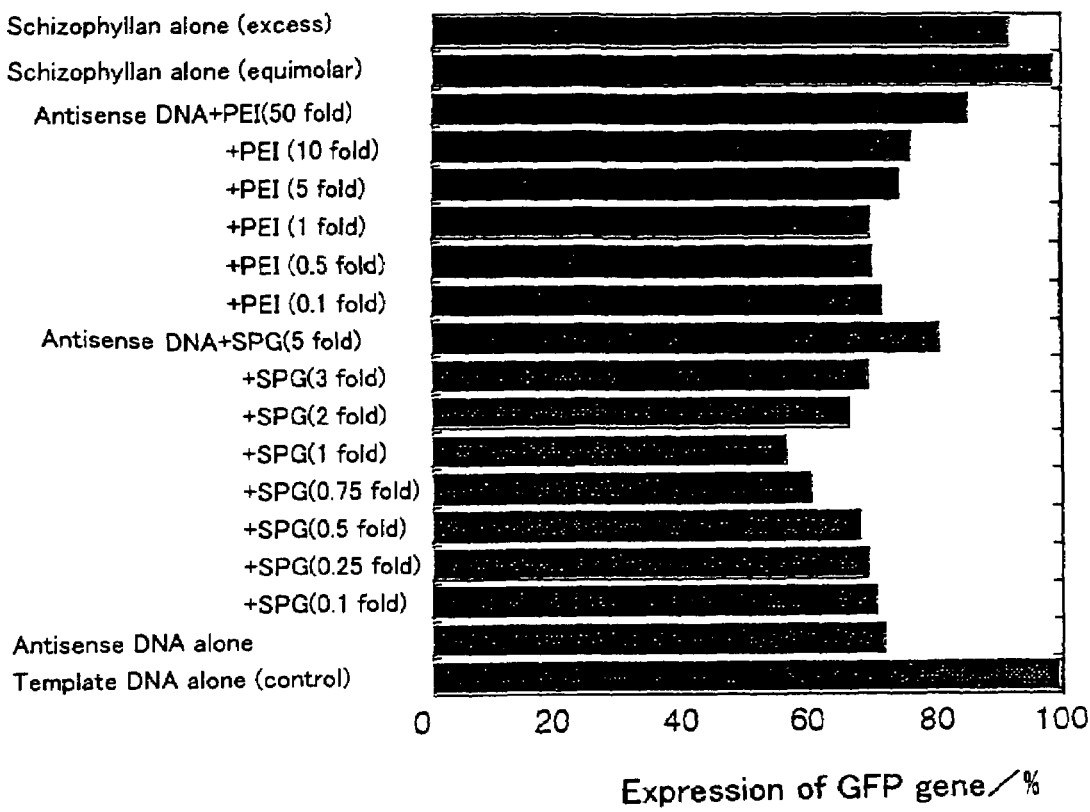
FIG. 10 illustrates the results of experiments for evaluating antisense effect by the modified schizophyllan-antisense DNA complex according to the present invention.

The results are shown in FIG. 10. As can be seen from the figure, the addition of the antisense DNA resulted in a decrease in the intensity of the fluorescence due to the expression of GFP. In addition, the transcription and translation of GFP reporter gene were more suppressed with increasing amount of SPG added to the antisense DNA. It is believed that such antisense effect is reliably achieved through the release of the antisense DNA from the antisense DNA-SPG complex in which the antisense DNA is protected by SPG. It is noted that the addition of SPG in an amount of two-fold or more did not produce any further suppression effect. This is presumably because the formation of the complex proceeds on a stoichiometric basis and an addition exceeding the stoichiometrically needed amount does not provide any further effect or because an excess addition may result in a decrease in the solubility.

By contrast, the addition of PEI did not achieve any substantial effect over the case where PEI was not added, and even an increase in the amount thereof did not result in any enhanced suppression. It is thus evidenced that the use of the polysaccharide of the present invention is quite advantageous. It is further noted that the excess addition of PEI lowered the suppression effect. This is presumably because the excess cationic charges on PEI resulted in insolubilization of the complex, lowering of the releasability or non-specific binding due to the electrostatic interaction. Equimolar or excess addition of the schizophyllan to the antisense DNA caused substantially no decrease in the fluorescence intensity, suggesting that the schizophyllan alone exerted almost no influence on the transcription and translation of GFP reporter gene.

Example 7

Change in Antisense Effect with the Elapse of Time

The solution of the schizophyllan in dimethyl sulfoxide was added to the solution containing an antisense DNA having a sequence of CTTTAAGAAGGAGATATACAT (SEQ ID NO:1) with the 3' end thereof being linked to forty dA's as used in Examples 5 & 6 (referred to as antisense DNA), or another antisense DNA having a sequence of CTTTAA-GAAGGAGATATACAT (SEQ ID NO:1) with each end thereof being linked to forty dA's (referred to as antisense DNA-2). Specifically, the modified schizophyllan was added to each antisense DNA's in an amount of 1.0 fold on a molar basis, in the manner of Example 5. The resultants were matured in a refrigerator for five days, and then subjected to ultrafiltration with a membrane (having an exclusion limit of 3000) to remove the dimethyl sulfoxide so as to form the complexes (referred to as +SPG complexes). The testing for antisense effect was performed in the same manner as in Example 6. Thus, each reaction solution was prepared by adding each of the DNA's or each of the SPG complexes to the mixture containing the template DNA and the transcription/translation solution. The transcription and translation reaction was carried out, while measuring fluorescence intensity due to GFP after 0, 0.5, 1.0, and 3.0 hours after the initiation of the reaction. The data were normalized in such way that the fluorescence intensity at 507 nm after the 3.0 hour with the case of no DNA addition was 100.

Figure 11:
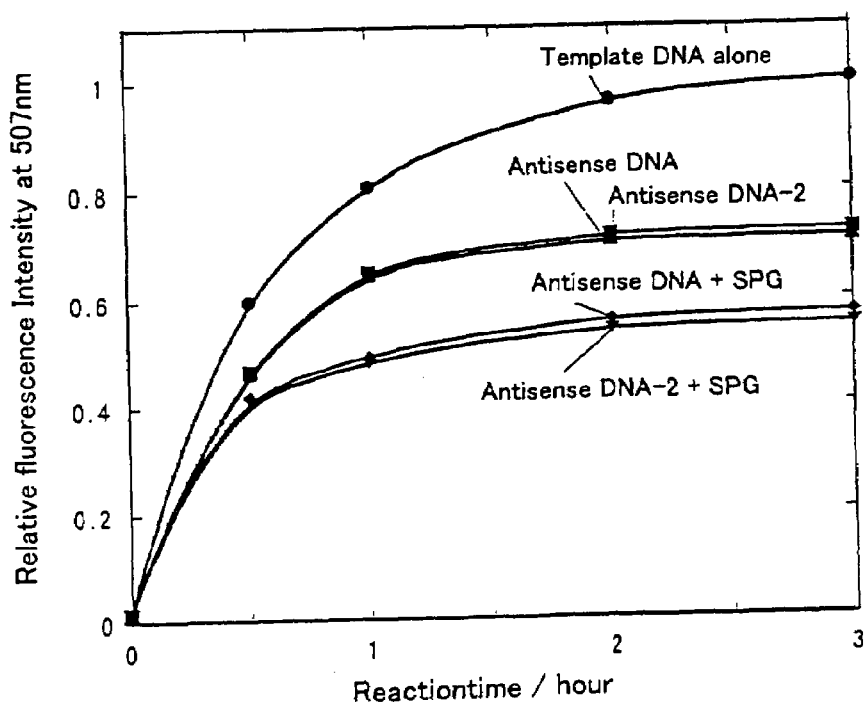
FIG. 11 is a representation of experimental results showing the change with the elapse of time in the function of the modified schizophyllan as a gene carrier according to the present invention.

The results are given in FIG. 11. As can be seen from the figure, after the elapse of 30 minutes from the initiation of the reaction, +SPG complexes showed decreased fluorescence intensities at 507 nn due to the expression of GFP, as compared with the references, suggesting that the former enhance the suppression of the GFP expression. No substantial change was observed in the antisense effect up to the three hours. It is also noted that there was no difference in the antisense effect between the termini of the antisense chains to which the dA's were linked.

Example 8

Evaluation of Resistance to Nuclease by Complex

The solution of the modified schizophyllan of the present invention in dimethyl sulfoxide was added to the buffer solution containing the antisense DNA as described Examples 5 and 6. The mixture was matured in a refrigerator for five days, and then subjected to ultrafiltration with a membrane (having an exclusion limit of 3000) to remove the dimethyl sulfoxide. To the resultant was added S1 Nuclase (Takara Shuzo), a nuclease for specifically decomposing single-stranded nucleic acid, in an amount of 3 U so that the final concentration of the schizophyllan was $6.1 \times 10^{-4}$ M, and that of zinc sulfate was 10 mM. Then, the decomposition of the antisense DNA, in the presence of the schizophyllan (referred to as +SPG), was followed by measuring the absorbance at 260 nm, due to the nucleic acid on a spectrophotometer (Jasco). The measurements were also made under conditions where no schizophyllan was present (as reference).

Figure 12:
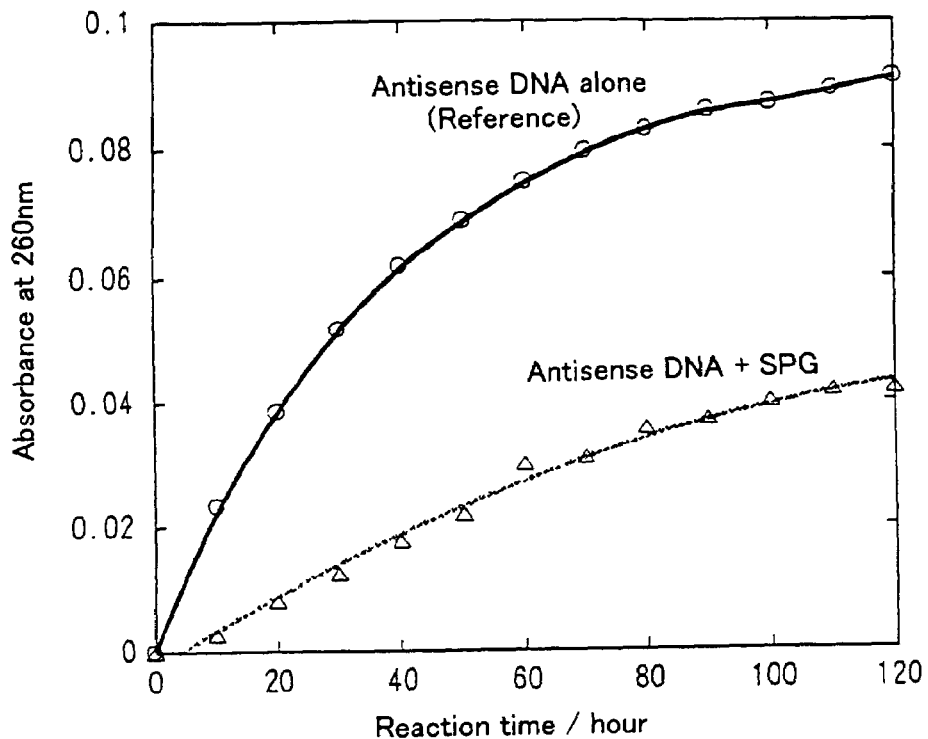
FIG. 12 is a representation of experimental results showing that the nucleic acid-polysaccharide complex of the present invention is resistant to nucleotides.

The results are shown in FIG. 12. The degree of increase in the absorbance at 260 nm was clearly smaller in the case of +SPG as compared with the reference. This is presumably because the formation of the antisense DNA-SPG complex brought about resistance to the nuclease, thereby resulting in an enhanced antisense effect as in Example 7.

Example 9

Enhanced Antisense Effect Due to Resistance to Nuclease

The modified schizophyllan of the present invention in dimethyl sulfoxide was added to the solution containing the antisense DNA as described in Example 5 and 6. Specifically, the modified schizophyllan was added to the antisense DNA in an amount of 1.0 fold on a molar basis, in the manner described in Example 5. The resultant was matured for five days in a refrigerator, and then subjected to ultrafiltration with a membrane (having an exclusion limit of 3000) to remove the dimethyl sulfoxide so as to form the complex (referred to as +SPG complex). The antisense effects were evaluated in the same manner as in Examples 6 and 7. Thus, a reaction solution was prepared by adding the antisense DNA (as reference) or the SPG complex to the mixture containing the template DNA, the transcription/translation solution and magnesium chloride. To each of the reaction solutions thus prepared was added Exonuclease I (Pharmacia), a nuclease for single-stranded DNA, in an amount of 1 U. Then the transcription and translation reaction were performed at 37° C., followed by measurement of fluorescence due to GFP. The measurement of fluorescence was also made with the sample not containing the antisense DNA, with the fluorescence intensity thereof being normalized as 100 (as reference).

Figure 13:
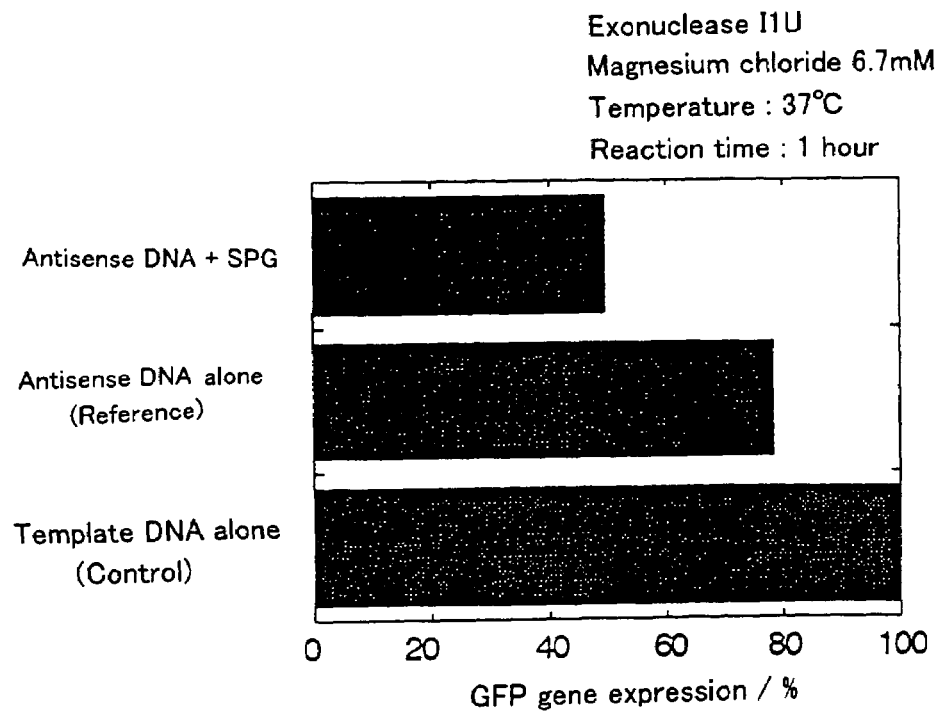
FIG. 13 is a graphical representation showing that the nucleic acid-polysaccharide complex of the present invention is resistant to nuclease resulting in increased antisensing effects.

The results are shown in FIG. 13. As can be seen from the figure, the SPG complex showed a decreased intensity in the fluorescence at 507 nm due to the expression of GFP, as compared with the reference, in which the difference therebetween was larger than that observed in Example 6. It was thus evidenced that the complex will serve to suppress efficiently the GFP expression.

Example 10

Association of Complex and Substitution with Complementary Strand

In a similar manner to that described in Example 3, there was prepared a mixture (1200 μl) of the modified schizophyllan of the present invention and poly (dT). In sodium chloride solutions in water with varying concentration in the range of 0.05M to 0.5M, there were dissolved poly(dA) in equimolar amounts with poly(dT) contained in the above-prepared mixture. Each of the poly(dA) solutions was added dropwise to said mixture containing poly(dT). On measuring the resultant solutions for the CD spectra after three hours while being kept at 10° C., there were observed well-known CD spectra due to the poly(dT)-poly(dT) double helix. Ultraviolet absorption spectrum measurements also gave an absorption coefficient attributable to a typical double-strand poly(dA)-poly(dT) complex (cf. Experimental Chemistry Series, Nucleic Acid II). Thus, the modified schizophyllan-poly(dT) complex of the present invention was decomposed by the presence of poly(dA), leading to the formation of a new complex, the poly(dA)-poly(dT) complex. This example illustrates that the presence of a complementary strand causes a rapid hybridization.

Example 11

Synthesis of Cholesterol-Modified Schizophyllan

The hydroxyl group of cholesterol (1 mg) was allowed to react with excess phosgene (triphosgene) to chloroformate ester (yield: 80%). The chloroformate ester-substituted cholesterol was then allowed to react with equimolar ethylene diamine. The cholesterol derivative thus prepared and containing an amino group was introduced into the single-stranded schizophyllan (s-SPG) in the manner described in Example 1. The rate of introduction was regulated through the amounts of the starting cholesterol derivative, which can be determined by elemental analysis. There were obtained cholesterol-introduced schizophyllans with the rate of introduction being 2 mol %, 10 mol % and 30 mol %, which are referred to as C-s-SPG-$O_2$, C-s-SPG-10 and C-s-SPG-30, respectively.

Example 12

Synthesis of Peptide-Modified Schizophyllan

As a example of amino acid-based functional group, integrin-binding peptide (cystein-tyrosine-glycine-glycine-arginine-glycine-aspartic acid-threonine-proline) was introduced into the schizophyllan. Specifically, 1 mg of the peptide, with the C-terminus thereof being protected by an esterification, and the triple helix schizophyllan following the periodate oxidation as described in Example 1, were added to 20 mL DMSO, followed by stirring for an hour at room temperature. The resultant was then subjected to treatment with a large amount of sodium borohydride, reprecipitation with methanol, and lyophilization. The sample thus obtained is herein referred to as InG-s-SPG.

Example 13

Synthesis of Intercalator-Modified Schizophyllan

The schizophyllan was chemically modified with an acridine derivative: In accordance with the reaction scheme illustrated in FIG. 6, an aminoalkane carboxylic acid (the one shown in FIG. 6 in which $R_x$ is $C_2H_4$), as the spacer moiety, was introduced into acridine, using dicylohexyl carbodiimide as the condensation agent. The aminated acridine thus obtained was subjected to the reductive amination reaction, as in Example 1, together with the single-stranded schizophyllan following the periodate oxidation. The sample thus prepared is herein referred to as Ac-s-SPG. Elemental analysis showed that the rate of introduction was 6%.

Example 14

Confirmation of Complex Formation

The formation of complexes of the modified schizophyllan, as prepared in Example 11 and 13, with nucleic acids was examined through CD spectrum measurement, the fluorescence depolarization method, and gel electrophoresis, An outline of the conditions and methods for the experiments follows:

The measurements of CD spectra were carried out in the same manner as in Comparative Example 2. The fluorescence depolarization method was carried out on JACSFP-715. Marking of the modified schizophyllans with a fluorochrome was conducted in the manner described in Example 15. The solutions were diluted for the fluorescence measurements and the complex formation was judged at the point where the P value indicating the degree of fluorescence depolarization was 50% of that of the schizophyllan marked with the fluorochrome. The gel electrophoresis was examined with agarose gel, each gel being stained with gelstar (FMC: Bioproduct) following a three-hour migration. Almost no migration occurs upon the formation of a complex, whereas free nucleic acids continue to migrate. The results are summarized in Table 3.

TABLE 3

|  | Poly(C) | Single-stranded DNA as described in Example 5 but having no poly(dA) tail | DNA from salmon's sperm |
|---|---|---|---|
| C-s-SPG-02 | ○ | ○ | X-Δ |
| C-s-SPG-10 | ○ | ○ | ○ |
| C-s-SPG-30 | ○ | ○ | ○ |
| Ac-s-SPG | ○ | ○ | ○ |
| Comparative: Unmodified single-stranded schizophyllan | ○ | X | X |

○ Complex formation
X No complex formation

Example 15

Introduction of Complexes into Cells

Hep G2 cells, human hepatic cells (available from American Type Culture Collection: ATCC), were cultured in Eagle's minimum essential medium (EMEM medium: Sigma) supplemented with 10% fetal bovine serum (FBS: Wako) at 37° C. with 5% $CO_2$, from which there was obtained Hep G2 cell culture supernatant. InG-s-SPG, as prepared in Example 12, and s-SPG were each dissolved in anhydrous DMSO and the resultant solutions were each added with a small quantity of fluoresceine isocyanate to provide the saccharide chains with a fluorescence marker. The samples thus prepared are herein referred to as InG-s-SPG-FITC and s-SPG-FITC, respectively. The antisense DNA used in Example 6, CTTTAAGAAGGAGATATACAT (SEQ ID NO:1)-(dA)40, was modified at the 3'end thereof, with rhodamine, as a marker. The DNA sample thus prepared is herein referred to as R-DNA1.

R-DNA1 plus InG-s-SPG-FITC and R-DNA1 plus s-SPG-FITC were each dissolved in a DMSO solution. In each case the polysaccharide was added to 1.5 times excess of the stoichiometric amount: This reliably formed the complexes and it was confirmed that the excess polysaccharide not used for the complex formation did not at all adversely affect the system. The formation of the complexes was monitored by gel electrophoresis. The resultant samples were each added to the Hep G2 cell culture supernatant, followed by culturing at 37° C. with 5% $CO_2$.

At four hours after the initial contact of the samples with the cells, the culture medium was discarded, followed by washing the cultures with a phosphate buffer and fixation of the cells with 4% paraformaldehyde. The resultants were observed under a fluorescence microscope (Olympus IX70-22PH). As a result, fluorescent cells stained with fluoresceine in the case of the addition of InG-s-SPG-FITC were observed at 10 to 100 times the number observed in the case of the addition of s-SPG-FITC, no peptide-modified sample. Monitoring of the degree of the antisense DNA transferred into the cells through the rhodamine coloration also indicated that the addition of InG-s-SPG-FITC was 10 to 100 times higher that in the case of the addition of s-SPG-FITC, no peptide-modified sample.

Example 16

Introduction of Complexes into Cells

C32 cells, human melanoma cells (available from ATCC), were cultured in EMEM medium supplemented with 10% FBS and 10% nonessential amino acids at 37° C. with 5% $CO_2$. The resultant thus obtained is herein referred to as C32 culture cell supernatant. The 17% amino group-modified cationic schizophyllan prepared in Example 1 (herein referred to as N-s-SPG17) was provided with the fluorescence marker in the same manner as in Example 15. The resultant thus obtained is herein referred to as N-s-SPG17-FITC. R-DNA1, the rhodamine-modified nucleic acid sample, was prepared in the same manner as in Example 15, and a complex of N-s-SPG17-FITC and R-DNA1 was formed. The complex was added to C32 cell culture supernatant, followed by culturing at 37° C. with 5% $CO_2$. At three hours after the initial contact of N-s-SPG17-FITC with the cells, the culture was subjected to cell fixation for examination under a fluorescence microscope. There was observed fluorescence emission on the cell surfaces, from which it was confirmed that N-s-SPG17-FITC was introduced into the cells. In addition, the rhodamine coloration indicated that the degree of the antisense DNA transferred into the cells in the case of the addition of N-s-SPG-FITC was 10 to 100 times larger than that in the case of the addition of s-SPG-FITC, non-modified sample.

SEQUENCE LISTING

<110> Japan Science and Technology Corporation,
<110> KIMURA Taro
<110> MIZU Masamui
<120> Gene carrier utilizing polysaccharide and method for making same
<130> P0266T-PCT
<150> JP P2001-069655
<151> 2001-03-13
<150> JP P2001-130705
<151> 2001-04-27
<160> 1
<210> 521
<211> 21
<212> DNA
<213> Artificial Sequence
<400 > 1
ctttaagaag gagatataca t

SEQUENCE LISTING

<160> NUMBER OF SEQ ID NOS: 1

<210> SEQ ID NO 1
<211> LENGTH: 21
<212> TYPE: DNA
<213> ORGANISM: Artificial
<220> FEATURE:

```
<223> OTHER INFORMATION: Antisense DNA which is complementary to  the
      sequence of the lysome binding site of the T7 promoter carried by
      the T7 phage

<400> SEQUENCE: 1
ctttaagaag gagatataca t                                              21
```

The invention claimed is:

1. A gene carrier composed of a complex in which a single-stranded nucleic acid is bound to a double-stranded β-1,3-glucan wherein the β-1,3-glucan has at least one 1,6-glucopyranoside branch per repeating unit of polysaccharide and is selected from schizophyllan, lentinan, grifolan, and scleroglucan, and wherein at least some of 1,6-glucopyranoside branches are chemically modified to be functionalized with nucleic acid-binding functional groups which are cationic functional groups formed by reaction of the polysaccharide with chain or cyclic compounds containing at least one primary or secondary amino group, wherein the chemical modification is carried out by periodate-oxidizing the 1,6-glucopyranoside branches and then reductive-aminating the periodated 1,6-glucopyranoside branches to impart the nucleic acid binding functional group thereto, and wherein the 1,6-glucopyranoside branch which has been functionalized with the nucleic acid-binding groups is expressed by the following general formula (1):

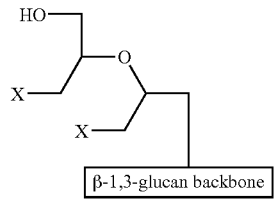
(1)

wherein the two X's are the cationic functional groups and are identical or different.

2. The gene carrier of claim 1, wherein the nucleic acid-binding functional groups are introduced at a rate of at least 0.1 mol % and up to 50 mole % based on the repeating unit of the polysaccharide.

3. The gene carrier of claim 1, wherein the β-1,3-glucan has a molecular weight of at least 2000.

4. The gene carrier of claim 1, wherein the nucleic acid is an antisense DNA.

5. The gene carrier of claim 1, wherein the β-1,3-glucan comprises schizophyllan.

* * * * *